United States Patent [19]

Kronman et al.

[11] 4,135,302

[45] Jan. 23, 1979

[54] ENDODONTIC THERAPEUTIC DEVICE AND PROCEDURES

[75] Inventors: Joseph H. Kronman, Canton; Melvin Goldman, Worcester, both of Mass.

[73] Assignee: National Patent Development Corporation, New York, N.Y.

[21] Appl. No.: 554,222

[22] Filed: Feb. 28, 1975

[51] Int. Cl.² ............................................. A61C 5/02
[52] U.S. Cl. ....................................................... 32/57
[58] Field of Search ................. 32/57, 40 R; 128/239, 128/251

[56] References Cited

U.S. PATENT DOCUMENTS

| | | | |
|---|---|---|---|
| 1,573,749 | 2/1926 | Ross, Jr. ................... | 128/239 |
| 3,035,351 | 5/1962 | Hirsch ..................... | 32/40 R |
| 3,745,655 | 7/1973 | Malmin ..................... | 32/57 |
| 3,783,867 | 1/1974 | Summersby et al. ........... | 128/251 |

Primary Examiner—Robert Peshock
Attorney, Agent, or Firm—Cushman, Darby & Cushman

[57] ABSTRACT

A device and procedures for endodontic therapy. An elongated flexible tubular member having a plurality of axially directed orifices formed in the distal end thereof has the proximal end thereof adapted to be connected to a source of supply of liquid. The liquid may be chemically active against necrotic tissue such as a solution of sodium hypochlorite. The distal end of the device is inserted into a root-pulp channel during a root canal procedure and liquid is delivered laterally against the walls of the channel thereby performing a mechanical scrubbing action and providing chemical action. The distal tip of the tubular member is closed off so as to prevent any liquid being expressed directly upon the root apex.

2 Claims, 4 Drawing Figures

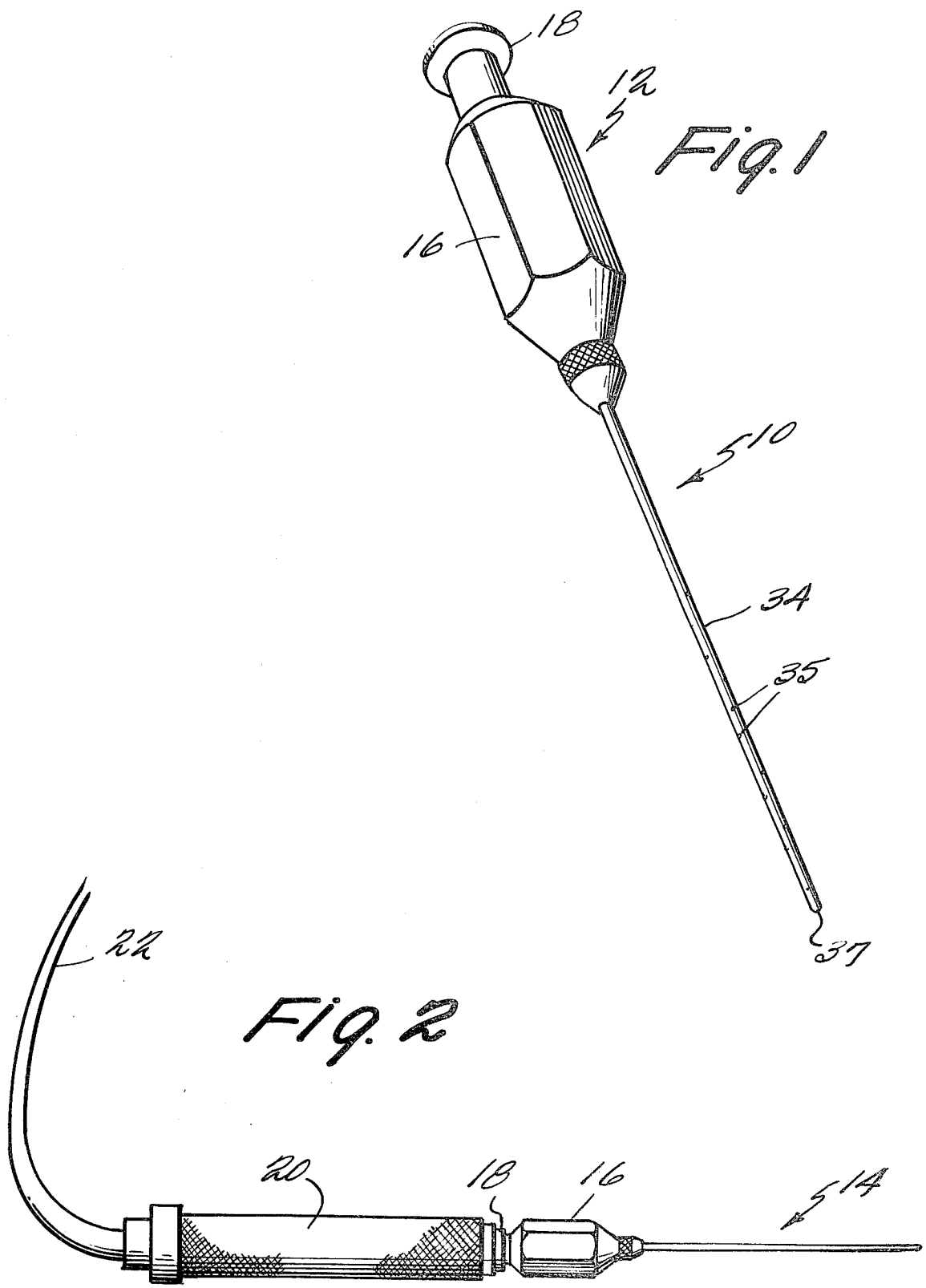

ENDODONTIC THERAPEUTIC DEVICE AND PROCEDURES

BACKGROUND AND SUMMARY OF THE INVENTION

The invention relates to a device and a procedure for the flushing and/or cleansing of the root-pulp channel of a tooth, especially in a root canal procedure in general preparation of the root canal for filling. It has long been recognized that for proper execution of endodontic therapy proper irrigation and preparation of the root canal must take place along with removal of the necrotic material from the canal. In the past this has generally been accomplished by introducing a liquid, such as water, sodium hypochlorite, or the like, into the canal in the longitudinal direction of the canal. Exemplary prior art devices and procedures for accomplishing this are disclosed in U.S. Pat. Nos. 3,816,921 and 3,747,216 and Swiss Pat. No. 297,607. Such prior art devices and procedures have not been entirely satisfactory in (a) quickly and efficiently cleansing and flushing the lateral walls and irregularities of the root-pulp channel, and (b) preventing periapical involvement as the result of liquid being expressed through the root apex (apical foramen). Recent research has shown the root canal, after thorough mechanical instrumentation, is still highly irregular and many areas of the root canal are not reached or touched by the instruments currently in common use.

According to the teachings of the present invention, an improved apparatus and an improved procedure are provided for endodontic therapy. An elongated tubular member is provided having a plurality of axially extending orifices formed in the distal end thereof. The member is adapted to be connected to a source of supply of a suitable cleansing and/or flushing liquid, which liquid is delivered through the tubular member orifices and thereby laterally directed against the walls of the root-pulp channel of the tooth receiving endodontic therapy. The laterally directed liquid exerts a mechanical scrubbing action against the channel walls resulting in efficient and quick flushing of the whole lateral area thereof. The distal tip of the member is closed off so as to prevent apically directed fluid streams which are present in the prior art and which result in increased chances of periapical involvement compared to the present invention.

In practicing the method according to the present invention, after removal of decayed pulp from a tooth, a spray of liquid is laterally directed against the walls of the root-pulp channel. In addition to mechanical scrubbing action, chemical removal of any remaining necrotic material ensues while the healthy tooth portions are not affected. Suitable liquids include, but are not limited to, sodium hypochlorite. Any irrigating solution commonly used in endodontic treatment can be employed, e.g., water, saline, aqueous solutions of sodium hypochlorite, of hydrogen peroxide, of urea peroxide, and others. An antiseptic solution or an antibiotic solution depending upon the particular circumstances, can also be used.

It is the primary object of the present invention to provide improved apparatus and procedures for endodontic therapy. This and other objects of the invention will become clear from an inspection of the detailed description of the invention, and from the appended claims.

BRIEF DESCRIPTION OF THE DRAWINGS

FIG. 1 is a detail perspective view of an exemplary endodontic therapeutic device according to the present invention;

FIG. 2 is a diagrammatic view of an exemplary system for carrying out the teachings of the present invention;

DETAILED DESCRIPTION OF THE INVENTION

Figures 3, 4:
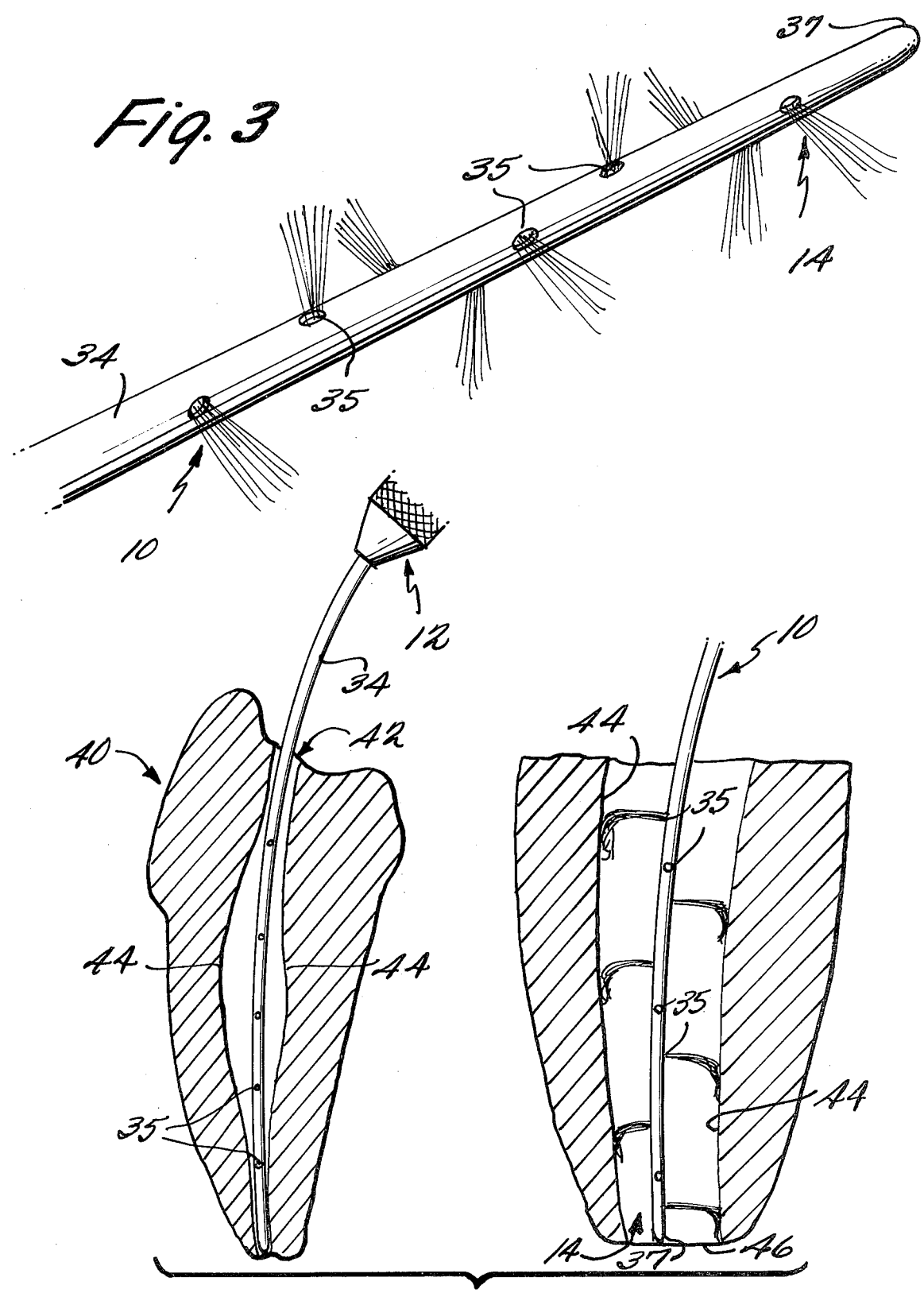
FIG. 3 is a detailed perspective view of the distal end of the device in FIG. 1 illustrating delivery of liquid therethrough.
FIG. 4 is a detailed diagrammatic view partially in cross-section showing the operation of the device of FIG. 1 in endodontic therapy.

An exemplary device according to the teachings of the present invention is shown generally at 10 in FIG. 1. This dental instrument 10 comprises a generally tubular member (having a longitudinal bore therein) with proximal end 12 and distal end 14. The proximal end 12 includes an enlarged portion 16 formed thereon adapted to be grasped by a human hand for facilitating movement of the device and/or to facilitate insertion of the open end 18 of the device 10 into a tubular handle member 20 any other handle suitable for the intended purpose.

As shown clearly in FIGS. 3 and 4, the tubular member 10 includes an elongated middle portion 34 connecting the proximal end 12 to the distal end 14. A plurality of axially directed orifices 35 are formed in the distal end 14 of the member 10. As shown most clearly in FIG. 4 these orifices serve to direct the liquid flowing through the longitudinal bore within the member 10 laterally against the walls 44 of the root-pulp channel 42 of a tooth 40 that is receiving endodontic therapy. The longitudinal bore through the member 10 is closed off at the distal tip 37 of the device 10, however, to prevent delivery of liquid directly upon the apical area 46 (apical foramen) of the tooth 40, and thereby minimize periapical involvement. Preferably, the member 10 is flexible so that it may be bent when inserted into a root canal 42 for most effective location therein.

In practicing the method according to the present invention, the normal preliminary procedures associated with endodontic therapy are carried out, such as opening of the access cavity, location and measuring of the opening of the radicular channel such as by X-ray techniques, and boring and removal of affected pulp and dentin. Then an operator holding the handle 20 with the device 10 attached thereto inserts the distal end 14 of the device 10 into the root-pulp channel 42. Liquid from any source is delivered laterally against the walls 44 of channel 42 via orifices 35 in device 10 to thereby provide a mechanical and chemical scrubbing action against the walls and remove any particles thereon.

It will thus be seen that according to the teachings of the present invention a device and procedure have been disclosed that provide for efficient and complete general cleansing of the whole root-pulp channel of a tooth receiving endodontic therapy while minimizing the chances of perapical involvement. Both a mechanical scrubbing action and a chemical action are provided for efficient tooth cleaning via a laterally directed liquid spray while the spray is confined within the root-pulp channel.

Thus all the objectives of the present invention have been accomplished. While the invention has been herein illustrated and described in what is presently considered to be the most practical and preferred embodiments, it will be obvious to one of ordinary skill in the art that many modifications may be made thereof within the scope of the invention, which scope is to be given the broadest interpretation of the appended claims so as to cover all equivalent devices and procedures.

What is claimed is:

1. An endodontic therapeutic process utilizing an elongated tubular member having a longitudinal liquid-transporting bore therein, and a plurality of lateral orifices in a distal end thereof and a solid distal tip to prevent the passage of liquid therethrough, said process comprising the steps of removing selected portions of dentin and pulp in a root-pulp channel, inserting the distal tip of said tubular member into said root-pulp channel so that the lateral orifices of said member are short of the tooth periapical area, exerting a mechanical action against the walls of the root-pulp channel by spraying a liquid through the lateral orifices in the distal end of said tubular member against the walls of the root-pulp channel while preventing the spraying of said liquid directly on the root apex to thereby minimize the chances of periapical involvement, and exerting a chemical action against the walls of the root-pulp channel by spraying said liquid laterally against walls thereof.

2. A procedure as recited in claim 1 comprising the further step of removing necrotic material from said root-pulp channel walls while not harming healthy tooth material.

* * * * *